(12) United States Patent
Eikmeier et al.

(10) Patent No.: US 10,132,792 B2
(45) Date of Patent: Nov. 20, 2018

(54) PORTABLE DIAGNOSTIC MEASUREMENT DEVICE FOR DETERMINING AT LEAST ONE ANALYTICAL PARAMETER OF A BODY FLUID

(71) Applicant: Roche Diabetes Care, Inc., Indianapolis, IN (US)

(72) Inventors: Heino Eikmeier, Lorsch (DE); Hans-Peter Haar, Wiesloch (DE); Joachim Hoenes, Zwingenberg (DE); Carina Horn, Biblis (DE); Ewald Rieger, Bobenheim-Roxheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 110 days.

(21) Appl. No.: 14/038,805

(22) Filed: Sep. 27, 2013

(65) Prior Publication Data

US 2014/0041443 A1    Feb. 13, 2014
US 2014/0238118 A9    Aug. 28, 2014

Related U.S. Application Data

(63) Continuation of application No. PCT/EP2012/001476, filed on Apr. 2, 2012.

(30) Foreign Application Priority Data

Apr. 5, 2011   (EP) .................................... 11002813

(51) Int. Cl.
*G01N 33/49* (2006.01)
*A61B 5/145* (2006.01)
(Continued)

(52) U.S. Cl.
CPC .......... *G01N 33/49* (2013.01); *A61B 5/1455* (2013.01); *A61B 5/1468* (2013.01);
(Continued)

(58) Field of Classification Search
CPC . A61B 5/14532; A61B 5/1455; A61B 5/1468; G01N 33/49
See application file for complete search history.

(56) References Cited

U.S. PATENT DOCUMENTS 5,279,294 A * 1/1994 Anderson .......... A61B 5/14532
600/322
2004/0192105 A1 * 9/2004 Boemmel ............ H01R 12/592
439/492

(Continued)

FOREIGN PATENT DOCUMENTS

CA        2303010 A1    10/2000
CN      101677794 A     3/2010
(Continued)

*Primary Examiner* — Manish S Shah
*Assistant Examiner* — Nathaniel Kolb
(74) *Attorney, Agent, or Firm* — Stinson Leonard Street LLP

(57) ABSTRACT

Disclosed herein are portable diagnostic measurement devices for determining at least one analysis parameter of a bodily fluid, in particular for determining an analyte concentration in a bodily fluid as can occur in blood glucose determinations. Also disclosed are analysis systems including the measurement device and at least one disposable test element. The test element can be designed as a carrier strip and can contact a receiving surface of the measurement device at least partially in a flat manner, where the receiving surface is arranged on a narrow side of the housing of the measurement device.

4 Claims, 15 Drawing Sheets

(51) Int. Cl.
*A61B 5/1455* (2006.01)
*A61B 5/1468* (2006.01)

(52) U.S. Cl.
CPC ...... *A61B 5/14532* (2013.01); *A61B 2560/04* (2013.01); *A61B 2560/0406* (2013.01); *A61B 2560/0418* (2013.01); *A61B 2560/0425* (2013.01)

(56) References Cited

U.S. PATENT DOCUMENTS

| | | | |
|---|---|---|---|
| 2007/0275476 A1* | 11/2007 | Charlton | A61B 5/14532 436/170 |
| 2008/0118399 A1* | 5/2008 | Fleming | A61B 10/0045 422/68.1 |
| 2010/0150777 A1* | 6/2010 | Nishida | A61B 5/14532 422/400 |
| 2010/0198107 A1* | 8/2010 | Groll | A61B 5/150022 600/583 |
| 2010/0331653 A1* | 12/2010 | Stafford | A61B 5/14532 600/365 |
| 2012/0045825 A1* | 2/2012 | Harttig | B01L 3/5023 435/287.1 |

FOREIGN PATENT DOCUMENTS

| | | | | |
|---|---|---|---|---|
| CN | 101969834 A | 2/2011 | | |
| CN | 101969835 A | 2/2011 | | |
| EP | 1048310 B1 | 11/2000 | | |
| EP | 1424040 A1 | 6/2004 | | |
| EP | 2116180 A1 | 11/2009 | | |
| EP | 2223746 A1 * | 9/2010 | ............ | B01L 3/5023 |
| JP | H06339473 A | 12/1994 | | |
| WO | 2000/040150 A1 | 7/2000 | | |
| WO | 2007/122380 A3 | 11/2007 | | |
| WO | 2009135863 A1 | 11/2009 | | |

* cited by examiner

PORTABLE DIAGNOSTIC MEASUREMENT DEVICE FOR DETERMINING AT LEAST ONE ANALYTICAL PARAMETER OF A BODY FLUID

CROSS-REFERENCE TO RELATED APPLICATIONS

This patent application is a continuation of Int'l Patent Application No. PCT/EP2012/001476; filed 2 Apr. 2012, which claims the benefit of EP Patent Application No. 11002813.1; filed 5 Apr. 2011. Each patent application is incorporated herein by reference as if set forth in its entirety.

TECHNICAL FIELD

The disclosure relates generally to medical diagnostics and engineering, and more particularly to portable diagnostic measurement devices for determining at least one analysis parameter of a bodily fluid. The disclosure further relates to an analysis system including the measurement device and at least one disposable (i.e., single-use) testing element.

BACKGROUND

Various forms of test elements for glucose determinations have been put into practice for sample application relative to a flat, rectangular strip geometry, especially so-called top-dosing test strips (i.e., application of a body fluid sample such as blood from above onto a test field that is mounted in a planar manner between both narrow sides of the measurement device).

In optical systems, a test field on a test strip can be measured through a hole in a carrier foil by means of absorption photometry measured in reflection. In general, the test strip is positioned above an optical measuring unit of the device, and a body fluid sample is applied to the test strip.

With top-dosing systems, the test strip is positioned in the middle of a housing trough to load it with the body fluid sample, and thus within the contour of the device. A user must place the body fluid sample from, for example, a finger onto the test strip in the middle of the device. In doing so, the user may have difficulty in seeing the target site behind the finger. Likewise, the body fluid sample may run onto the device or may even run onto or into the opening to the optical measuring unit, especially when a relatively large amount of sample hangs on the finger. Therefore, inaccurate application or excessive amounts of sample can contaminate the trough of the test strip holder or the optical measuring unit.

With outside-dosing systems, the test strip is removed, the body fluid sample is applied outside the device, and the test strip then is inserted back into the device. As with top-dosing systems, surfaces in outside-dosing systems may become contaminated because the complete test strip area can be used for sample application. In addition, the underside of the test strip can become unintentionally contaminated when, for example, the test strip is placed on a contaminated surface for sample application. Such contaminations can result in an erroneous measurement.

With out-of-meter-dosing systems, the body fluid sample is transported to the site of measurement through capillaries of the test strip. The required amount of body fluid sample, however, is considerably larger than with methods in which the sample is directly applied to the test field because firstly the capillaries have to be filled with sample. This disadvantage can be avoided with electrochemical test strips in which measurements can be carried out using common sample volumes by guiding the electrodes to the outside. However, the manufacture of such capillary test strips is relatively complicated due to the elaborate assembly process. Likewise, costs are proportionately high due to the high material costs for the bottom and cover foil.

For the foregoing reasons, there is a need for additional devices and systems for body fluid analysis having improved body fluid sample application characteristics and that avoid contamination.

BRIEF SUMMARY

An object of the present disclosure is to provide a measurement device and analysis system that provide simplified body fluid sample application and that avoid contamination while using cost-effective test elements. This object can be achieved by measurement devices and analysis systems as described herein.

In a first aspect, a measurement device can include a housing and a receiving surface for receiving a test element, which can be in the form of a carrier strip, where the receiving surface is located on a narrow side of the housing such that the test element lies at least partially in a planar manner on the receiving surface. In one embodiment, the test element can lie completely or substantially completely on the receiving surface.

In a second, related aspect, an analysis system can include a measurement device as described herein and at least one test element provided for single use therein, which can be in the form of a carrier strip. The test element therefore can be a disposable test element.

In embodiments of either aspect, the housing can have an essentially geometric shape, such as that of a cylinder with a base surface and a top surface. In one embodiment, the shape can be a straight cylinder. The base surface can form a rear side, and the top surface can form a front side of the housing. In addition, the base surface and the top surface can have essentially the shape of a polygon (i.e., a triangle, quadrangle or pentagon), an ellipse or a combination thereof. The lateral surface of the cylinder can be configured as narrow sides. If the base surface and the top surface have essentially the shape of a pentagon, the housing can have five narrow sides. In this manner, adjacent narrow sides can be separated from one another by edges that, for example, connect the edges of a polygon or, in other instances, connect the transition edges from the polygon to the ellipse of the base surface, with the top surface. In one embodiment, the edges can be rounded. In another embodiment, the edges of the narrow sides with the base surface and/or the top surface also can be rounded. Alternatively, the two edges can be rounded at one or more narrow sides in such a manner that they merge to form a new edge or to form an edgeless transition from the base surface to the top surface.

In some embodiments, the base surface and/or the top surface can have a convex or a concave curvature independently of one another. Equally, the narrow side on which the receiving surface is disposed can be curved relative to a plane that spans the receiving surface. With an elliptical base surface and a convexly curved base and top surfaces with rounded edges, the housing can have an oval shape. Alternatively, the base surface can be concave, and the top surface can be convexly curved parallel thereto.

In some embodiments, an entire narrow side can form the receiving surface. In other embodiments, a section of a narrow side can form the receiving surface. The narrow side or the section of the narrow side that forms the receiving surface, apart from an optional cover of the receiving surface, can be raised relative to adjacent or neighboring components of the measurement device and/or can have an exposed position.

In some embodiments, the measurement device can be used in medical laboratories. In other embodiments, the measurement device can be used by a patient to continuously monitor the patient's state of health (i.e., home-monitoring). For such purposes, simple handling is particularly important because only then is it possible to ensure that the necessary analyses are carried out regularly by the patient and that the accuracy of the analytical result is not impaired by handling errors. In this manner, the measurement device should be as small, light and robust as possible. In still other embodiments, the measurement device can be used in so-called near patient diagnostics (i.e., near-patient testing). As such, the measurement device can be a handheld device and/or mobile desktop device for the analysis of body fluids.

When the measurement device is a hand-held device, the base surface and/or the top surface are selected such that the measurement device can be held comfortably in one hand during the measurement. The edges can be rounded to obtain an ergonomic shape of the housing. When the measurement device is a desktop device, the base surface can include means for preventing slipping on smooth surfaces such as, for example, anti-slip knobs. When the measurement device is a mobile desktop device, the part of the housing on which the receiving surface is disposed can be angled relative to the rest of the housing in such a manner that it points towards the user and allows a comfortable application of the body fluid sample.

In some embodiments, a main axis of the measurement device can be in the plane of the device that is essentially parallel to the base surface and the top surface of the housing. The main device axis can be an imaginary straight line through the measurement device and can be used as a design and arrangement tool to describe the orientation and position of its structures. In this manner, it divides the front of the measurement device into two halves. When the receiving surface is angled relative to the rest of the housing, the measurement device can have a second device axis. The second device axis can lay in the same plane as the main device axis that divides the front of the measurement device and can be at an angle of about 20° to about 90°, about 30° to about 70°, or about 45° to about 60° to the device plane. In one embodiment, the second device axis can be essentially perpendicular to the plane dividing the front of the measurement device.

In some embodiments, the longitudinal axis of the receiving surface (also known as the axis of the receiving surface) can be essentially perpendicular to the plane dividing the front of the measurement device in which the main device axis lies. When the measurement device is a hand-held device, the axis of the receiving surface can be essentially perpendicular to the main device axis. When the measurement device is a mobile desktop device, the axis of the receiving surface can be essentially perpendicular to the second device axis that lies in the plane dividing the front of the measurement device. In another embodiment, when the second device axis lies perpendicular to the plane dividing the front of the measurement device, the axis of the receiving surface can be essentially parallel to the main device axis.

In some embodiments, the plane spanned by the receiving surface can be essentially perpendicular to the device plane.

As such, the device plane can be essentially parallel to the planes in which the base surface and the top surface of the housing lie, but the receiving surface plane can be essentially perpendicular to the plane that divides the front of the measurement device. In other embodiments, the plane spanned by the receiving surface can be rotated about the axis of the receiving surface. An angle of rotation can be in the range of about −35° to about 90°. The angle of rotation describes the rotation of the plane that is spanned by the receiving surface, about the longitudinal axis of the receiving surface relative to a surface that is perpendicular to the device plane. In this manner, a positive sign indicates a rotation in the direction of the top surface, and a negative sign indicates a rotation in the direction of the base surface. The angle of rotation corresponds to about 90° for a measurement device in which the housing member on which the receiving surface is disposed can be angled in such a manner relative to the remaining housing. The receiving surface therefore can be essentially parallel to the front side and the rear side of the measurement device. With an angled housing member, however, the angle of rotation can lie in the range of about 20° to about 70° or about 55° to about 65°. Without an angled housing member, the angle of rotation can lie in the range of about 0° to about −30° or about −10° to about −25°.

To avoid contamination by the applied body fluid sample, the entire receiving surface or a section of the receiving surface or at least the section of the receiving surface in the test field region is narrower than the intended test elements in the corresponding sections. In this manner, a test element that is positioned in the measuring position covers the receiving surface especially in the area of the test field.

In some embodiments, the measurement device includes a measuring unit to measure a measurement variable on a test element positioned in a measuring position (also denoted positioning end position). In this manner, the receiving surface can have a measuring opening such that the test field area of a test element located in the measuring position rests on the measuring opening. The test element can rest in such a manner that its test field area is at a defined distance from an optical measuring unit located below the measuring opening and thus in the interior of the device. The measuring unit also can include device contacts that can be in contact with sensor contacts of an electrochemical test element that can be located in the measuring position.

In some embodiments, the measured values of the measurement variable can be transmitted to an evaluation device to determine analytical data from measured values of the measurement variable.

In some embodiments, the measurement device can be used to determine glucose concentration in a body fluid such as, for example, a blood sample. In other embodiments, the measurement device can be used to determine analyte concentrations such as cholesterol and various blood coagulation parameters. As such, an analytical parameter is not necessarily to be understood as the concentration of a substance in the sample fluid but rather also can relate to other relevant analytical parameters (in particular in the medical field) such as the blood clotting time.

In some embodiments, elongate plastic strips can be used as a carrier layer of test elements, which also are known as biosensors. However, other shapes also are suitable, such as approximately quadratic plates.

The test element, which may be disposable, can be designed as a carrier strip. In this manner, at least one test field located on the carrier strip has an area for applying the body fluid sample. When the test element is in the measuring position on the receiving surface of the measurement device, the body fluid sample can be applied to the test field from the free upper side. When the test element is an optical test element, a change in color can be registered from the underside. When the test element is an electrochemical test element, a current can be measured from a plurality of electrodes.

In some embodiments, the test element can be a non-wipe test strip. As such, the body fluid sample, after being applied to the upper side of the test field, flows through an entire thickness of the test field consisting of several layers. In this manner, chemical reactions take place between the body fluid sample and the reagents contained in the test field. A resulting optically detectable change in a detection layer can be detected by reflection photometry from the underside of the test element. The base layer of the test element can have an opening for this purpose in the area of the test field.

In some embodiments, the test element can be divided longitudinally into three sections. In the first section, the test field defines a test field area. With respect to test elements having only one test field, the test field area can be bounded by the front edge and the rear edge of the test field. It also is possible for several test fields to be arranged one after another in a larger test field area on a test element. In this manner, the test field area extends in the insertion direction from the front edge of the first test field up to the rear edge of the last test field. The second section can be between the front end (with which the test element can be inserted, for example, into a holder of the receiving surface) and the test field area and can be referred to as the front section. The third section can be a handling section that extends between a handling end of the test element (opposite to the front end) and the test field area. In addition, the test element can have an opening in the front section near to the front end arranged centrally in the transverse direction of the test element.

In some embodiments, the measurement device can include a heating device to heat the test field of a test element positioned in the measuring position. In other embodiments, the measurement device can include a temperature-measuring device to determine the temperature of the test field of a test element positioned in the measuring position. The test field can be thermostated to a desired target temperature by means of an optional thermostating electronic device with the aid of the temperature-measuring device and the heating device.

In some embodiments, the measurement device can include one or more positioning devices to exactly position the test elements relative to, for example, a reflection photometer in an optical measurement or contacts in an electrochemical measurement. A positioning device improves accuracy of the measurement and simplifies handling. The positioning of the test element on the receiving surface relates to all three directions in space, namely to longitudinal and transverse directions of the test field, as well as to the vertical direction of the test field surface. The vertical distance between the surface of the test field and the measurement optics is a decisive parameter for an exact measurement. The vertical distance can be defined by the underside of the test element resting flat on the receiving surface. In other embodiments, the receiving surface also can include at least one device to position the test element.

For cost reasons, there is a trend towards making test field areas smaller and smaller. As such, the longitudinal and lateral positioning of the test elements can be carried out very exactly to be able to use the largest possible portion of the surface of the test field as a measuring area. An incorrect spatial alignment of test elements leads directly to a reduction of the effective measuring area and thus to a measuring error.

To prevent incorrect spatial alignment of test elements, the receiving surface can include at least one guide element on its longitudinal side to define a compulsory direction when the test element is inserted. The guide element also can be used for the lateral positioning in the measuring position. The guide element can be arranged on one side or both sides of the test element positioned in the measuring position. In other embodiments, the guide element can be arranged in the area of the measuring opening on both sides of the test element positioned in the measuring position.

In some embodiments, the at least one guide element can be in the form of guide rails that prevent a left-right displacement of the test element. In one embodiment, the guide rails can laterally cover the test element in front of and behind the test field to prevent a vertical displacement. In another embodiment, the receiving surface can have guide elements in the area of the front end and/or in the area of the handling end of the test element positioned in the measuring position. In yet another embodiment, the guide elements can be arranged on both sides such that only one positioning of the test element along the receiving surface is possible. In the case of a two-sided arrangement, the guide elements can be arranged on the left and right can be integrally formed and thus cover the receiving surface, particularly in the area of the front section. In an alternative embodiment, the guide elements can be arranged on one side in the area of the front end and/or in the area of the handling end of the test element positioned in the measuring position. In this case, the positioning process of the test element can take place at right angles to the receiving surface.

In some embodiments, the receiving surface can include a holder. The holder can be located under a flap with holding springs that press downwards onto the test strip.

For positioning purposes, the test element can have an opening in the area of its front end. The positioning device of the receiving surface has a rotatably mounted conical cam that can be rotated into its opening when the test element is inserted into the measurement device. In the positioning end position, the front end of the test element abuts against a stop and the rotatably mounted conical cam presses it down onto a support surface. In this manner, the cam engages in the opening in such a manner that force is applied to the test element in all three spatial directions resulting in a positioning.

In some embodiments, a test element having an opening at its handling end and at its front end can be used into each of which a clamping pin of the receiving surface engages. During the positioning process, the clamping pin at the front end can be firstly moved into the corresponding opening. Afterwards, the test element can be bent by actuating a movable cover such that the clamping pin located in the area of the handling end engages in the second opening. A spring engages with a second clamping pin in such a manner that the test element is placed under tensile stress in its longitudinal direction. This tensile stress presses the underside of the test element against a pressure plate on the receiving surface as a result of which the test field located on the upper side of the test element is in the desired position.

In other embodiments, the receiving surface can include a holder with guide elements. Here, the guide elements direct a test element in its transverse direction during insertion into the holder. The underside of the test field area of the test element in the measuring position rests on a receiving surface containing a measuring opening so that its test field area is at a defined distance from a measuring unit located below the measuring opening. To assist, the holder has a brace support projecting against the underside of the test strip and a pressing element that presses against the second side of the test strip in the measuring position between the brace support and the test field area. In this manner, the test element in the measuring position is under bending stress, which ensures a defined distance between the at least one test field and the measuring unit. An example of such a positioning device is described in EP Patent Application No. 97112668.5.

Bending the test element about a bending axis orientated at right angles to its longitudinal axis and parallel to its surface therefore can be used for positioning. The bending stress results from the elasticity of the base layer of the test element. Hence, test elements should be understood as all analytical elements (test carriers) which, due to their material properties and dimensions, have sufficient elasticity for such a positioning.

In some embodiments, the front section of the test element can include an opening. In this manner, the receiving surface has a spring-loaded holding pin at a corresponding position in the front section. The holding pin can be covered by a movable or pivoted or hinged cover. During positioning, the holding pin latches in the front opening of the test element. In other embodiments, the test element also includes a second opening in the test field area that corresponds with a positioning device at the measuring opening of the receiving surface of the housing of the measurement device. This positioning device can be a raised rim around the measurement opening. A left-right displacement of the test element is prevented by the positioning device hooking into the opening. Alternatively, or in addition, the measurement device can have guide rails in the test field area or in the handling area.

In some embodiments, the test element can be positioned and secured in a predefined measuring position solely by an insertion movement of the test element into the holder. In fact, a mechanism can be activated neither by the user nor by a drive of the evaluation device to secure the test elements in the evaluation device.

The exact positioning of the test field can be achieved without any parts pressing from above onto the test element in the vicinity of the test field area. In some embodiments, the receiving surface therefore has a first positioning device in the area of its front end and a second positioning device in the area of the measuring opening. The first positioning device can be a rotatably mounted conical cam, a clamping pin, a holding bolt, a spring-loaded holding pin or such like where the test element has a correspondingly configured opening in its front section. In one embodiment, the first positioning device is covered by a cover, which also can be part of the first positioning device (i.e., it can itself serve to position the test element). In another embodiment, the second positioning device consists of guide elements. In another embodiment, the receiving surface can be narrower than the test element positioned in the measuring position at least in the area of the measuring opening. A raised rim of the measuring opening can engage in the hole of the base foil of the test element and can be used as the second positioning device.

In some embodiments, the measurement device can include a cover to protect the receiving surface and in particular the measuring opening and/or a positioning device against contamination and the like during storage or transport of the measurement device. The cover can have a hinged, sliding, screwable or pluggable design. In one embodiment, the cover can be designed as a base of the measurement device when not in use.

These and other advantages, effects, features and objects of the invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
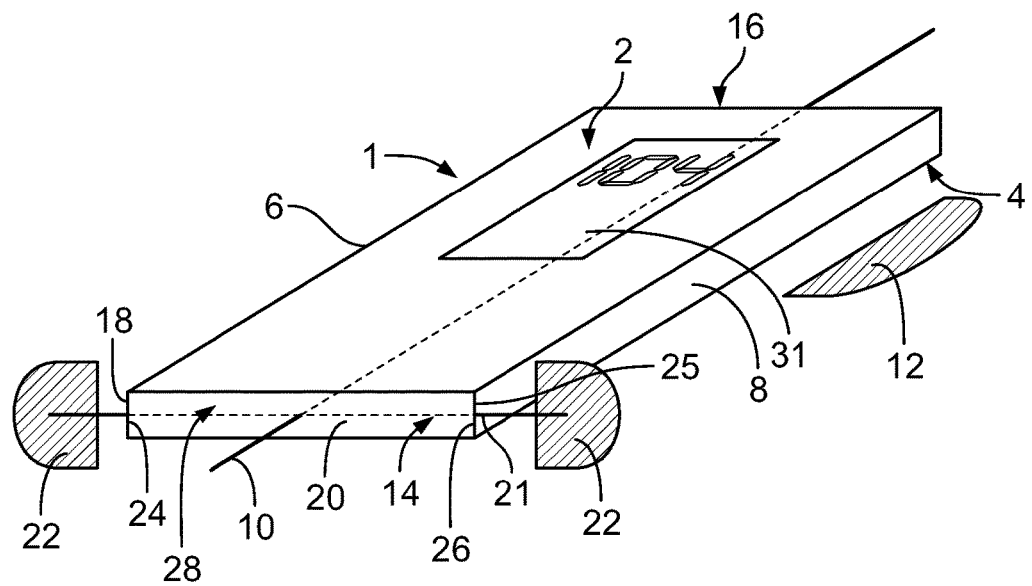
FIG. 1 shows a perspective schematic representation of an exemplary measurement device.

While the present invention is susceptible to various modifications and alternative forms, exemplary embodiments thereof are shown by way of example in the drawings and are herein described in detail. It should be understood, however, that the description of exemplary embodiments that follows is not intended to limit the invention to the particular forms disclosed, but on the contrary, the intention is to cover all advantages, effects, features and objects falling within the spirit and scope of the invention as defined by the embodiments above and the claims below. Reference should therefore be made to the embodiments above and claims below for interpreting the scope of the invention. As such, it should be noted that the embodiments described herein may have advantages, effects, features and objects useful in solving other problems.

DESCRIPTION OF PREFERRED EMBODIMENTS

The devices and systems now will be described more fully hereinafter with reference to the accompanying drawings, in which some, but not all embodiments of the invention are shown. Indeed, the devices and systems may be embodied in many different forms and should not be construed as limited to the embodiments set forth herein; rather, these embodiments are provided so that this disclosure will satisfy applicable legal requirements.

Likewise, many modifications and other embodiments of the devices and systems described herein will come to mind to one of skill in the art to which the invention pertains having the benefit of the teachings presented in the foregoing descriptions and the associated drawings. Therefore, it is to be understood that the devices and systems are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the devices and systems, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Devices and Systems

FIGS. 1 to 11 show embodiments in which the housing of the measurement device has approximately the geometric shape of a straight cylinder with a rectangular base and top surface. The geometric shapes of the base surface and top surface can be selected to lead to an ergonomically shaped housing.

Figure 2:
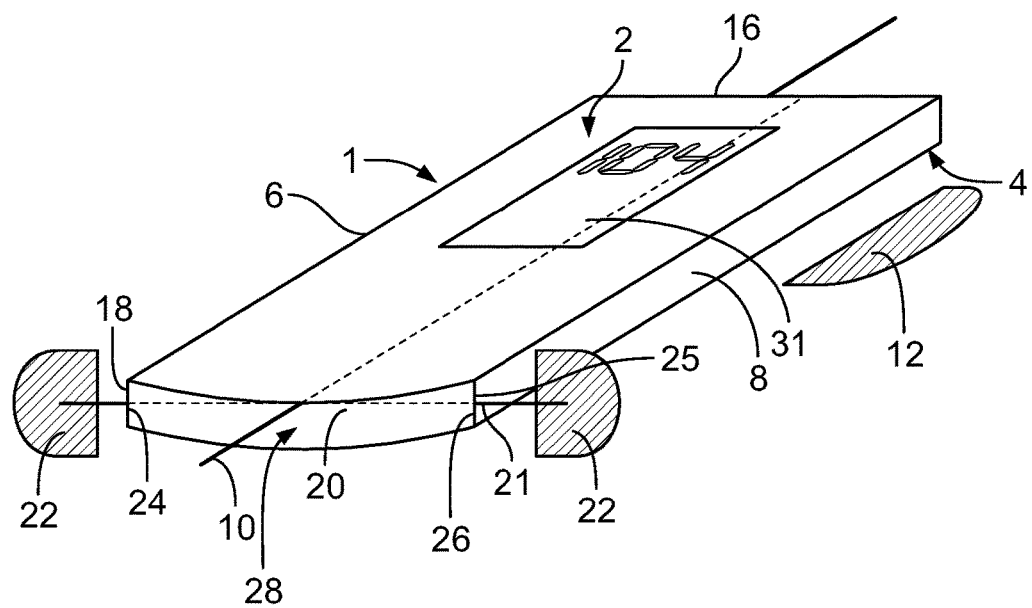
FIG. 2 shows a perspective schematic representation of another exemplary measurement device.

As shown in the FIGS., the housing 1 includes a top surface 2, and an opposing base surface 4, wherein the top surface 2 and the base surface 4 are arranged parallel to each other. Moreover, the housing 1 includes a first side 6 and an opposing second side 8. In embodiments, the first side 6 and the second side 8 are arranged parallel to the each other. The housing 1 includes a narrow side 14 and an opposing side 16 relative to the narrow side 14. As illustrated, the first side 6 defines a first end 18 of the narrow side 14 and the second side 8 defines a second end 25 of the narrow side 14. A receiving surface 20 is configured to extend up to and between the first end 18 and the second end 25. For example, FIGS. 1 and 2 show embodiments in which the entire narrow side of the housing 1 on which the receiving surface 20 is disposed forms the receiving surface 20. The axis 21 of the receiving surface 20 encloses an angle of about 90° with the main device axis 10. The plane 22, which is spanned by the receiving surface 20, is essentially perpendicular to the device plane 12 in FIGS. 1 and 2. As further shown in FIG. 2, the receiving surface 20 can be curved with respect to the plane 22, which is spanned by the receiving surface 20. Additionally, as illustrated in at least FIGS. 1-17, and 20, the receiving surface 20 includes a front end 24, a handling end 26, and an area 28 arranged between the front end 24 and the handling end 26, and along a longitudinal axis of the receiving surface 20. Moreover, the front end 24 and the handling end 26 are configured to position a test element 41 in the form of a carrier strip on the area 28 and parallel to the longitudinal axis.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, "essentially perpendicular" means that an angle in the range of about 70° to about 110°, about 80° to about 100°, or about 90° is enclosed. In contrast, "essentially parallel" means that an angle in the range of about −20° to about 20° or about −10° to about 10° is enclosed. Alternatively, it can mean parallel.

Figure 3:
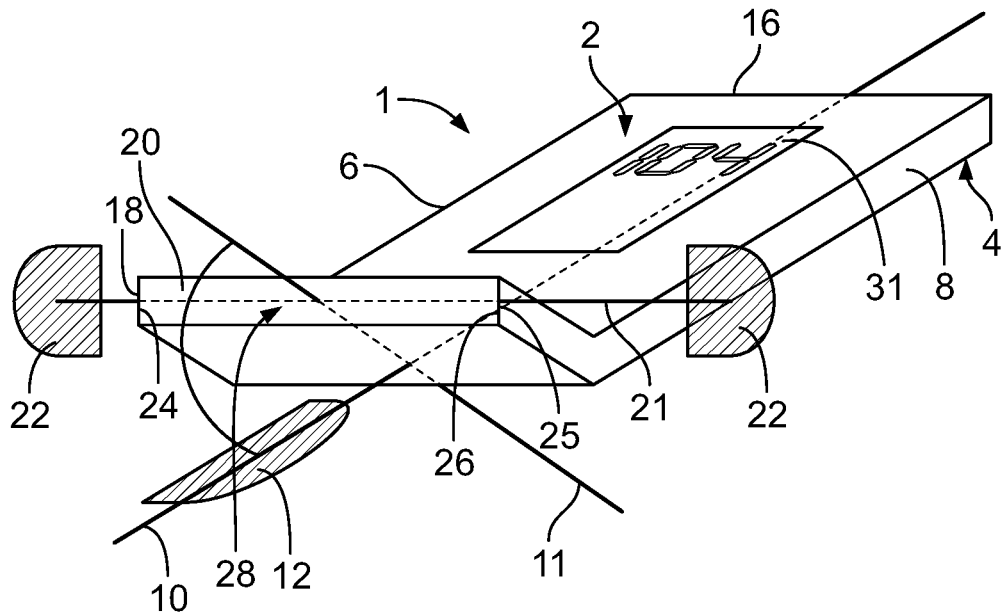
FIG. 3 shows a perspective schematic representation of another exemplary measurement device.
Figure 4:
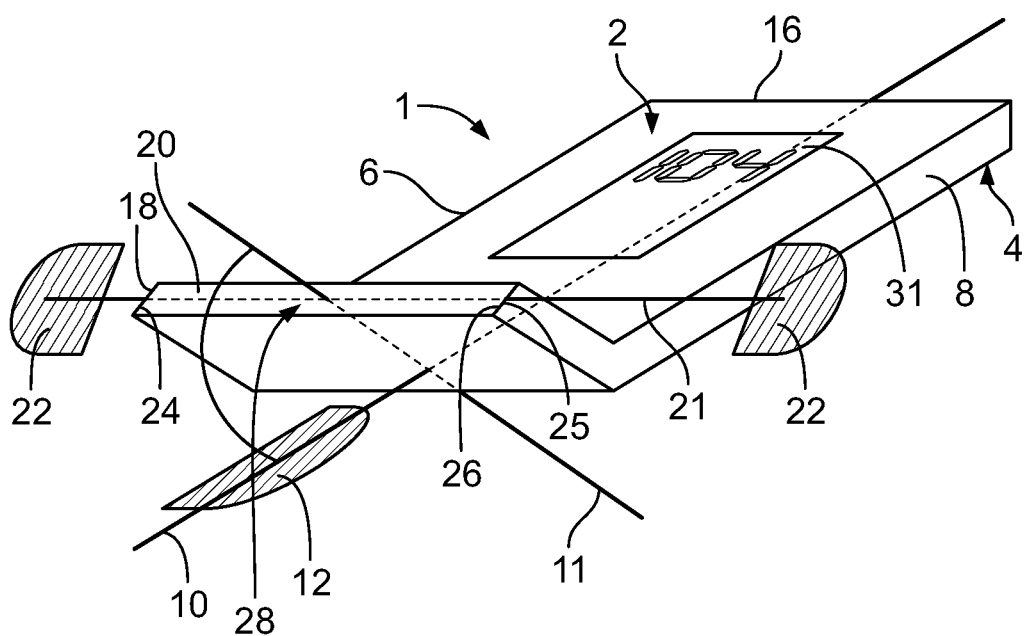
FIG. 4 shows a perspective schematic representation of another exemplary measurement device.
Figure 5:
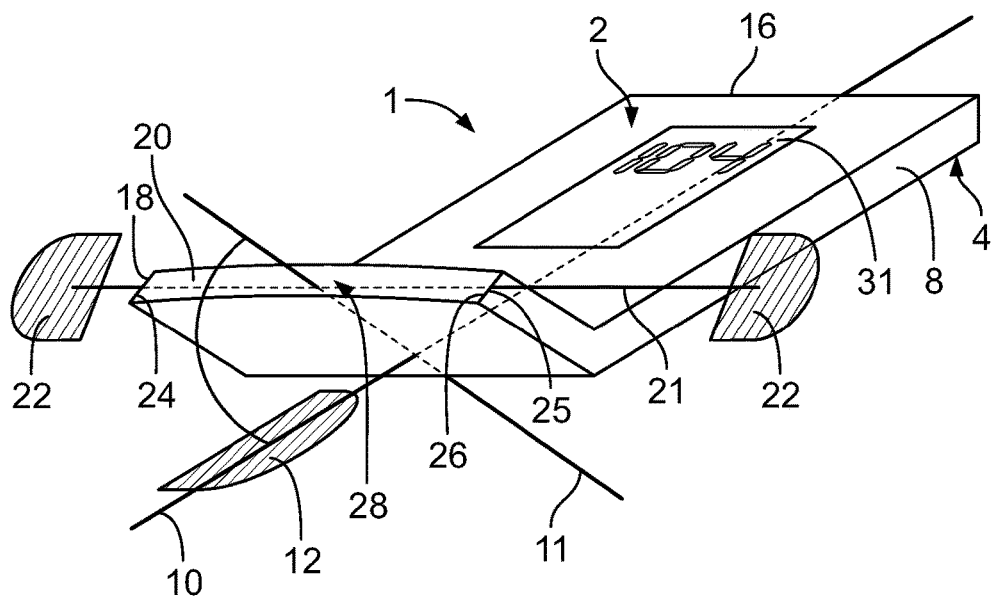
FIG. 5 shows a perspective schematic representation of another exemplary measurement device.

FIGS. 3 to 5 also show embodiments in which the entire narrow side of the housing 1 on which the receiving surface 20 is disposed, forms the receiving surface 20. The housing member on which the receiving surface 20 is disposed, however, is angled relative to the remaining housing 1. A second device axis 11 lies in the same plane dividing the front of the measurement device as the main device axis 10 and can enclose an angle of about 60° with the device plane 12. The axis 21 of the receiving surface 20 can enclose an angle of about 90° with the second device axis 11, which lies in the same plane dividing the front of the measurement device as the main device axis 10. The plane 22, which is spanned by the receiving surface 20, is essentially perpendicular to the device plane 12 in FIG. 3 and can enclose an angle of about 45° with the device plane 12 in FIGS. 4 and 5. As further shown in FIG. 5, the receiving surface 20 can be curved with respect to the plane 22, which is spanned by the receiving surface 20.

Figure 6:
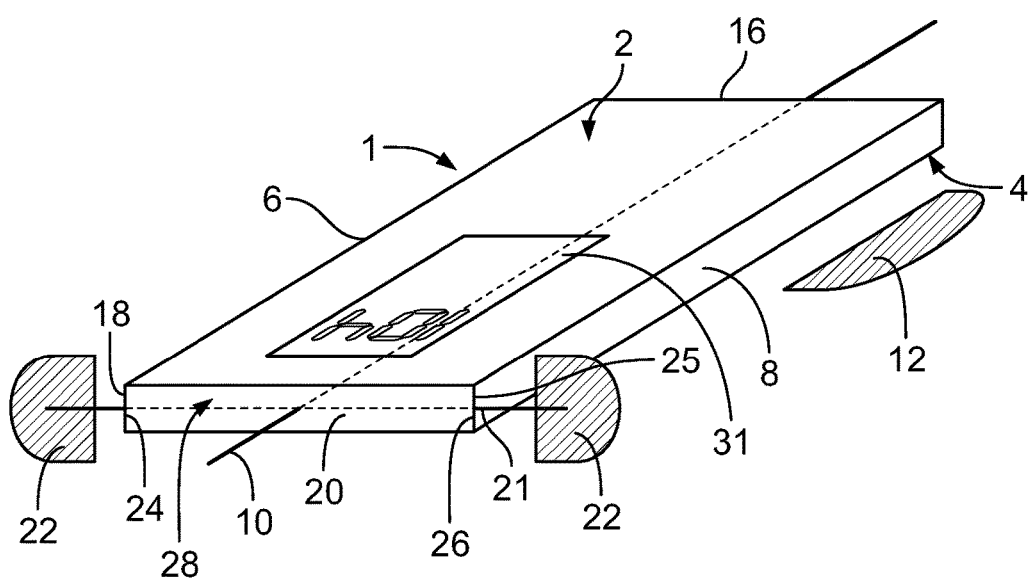
FIG. 6 shows a perspective schematic representation of another exemplary measurement device.

FIG. 6 shows an embodiment in which the receiving surface 20 is located on an opposing side of the embodiments shown in FIGS. 1 to 5 (e.g., near the display 31).

Figure 7:
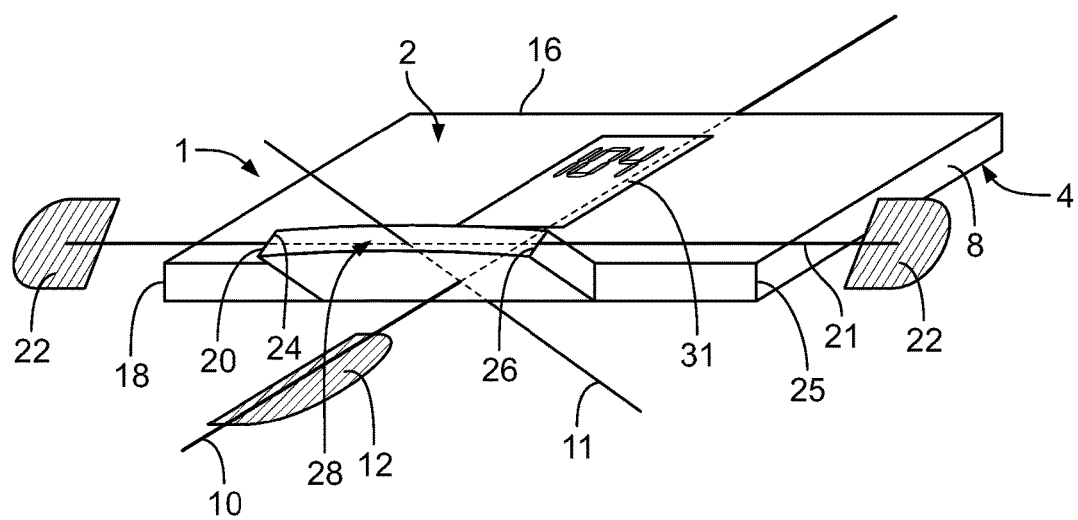
FIG. 7 shows a perspective schematic representation of another exemplary measurement device.
Figure 8:
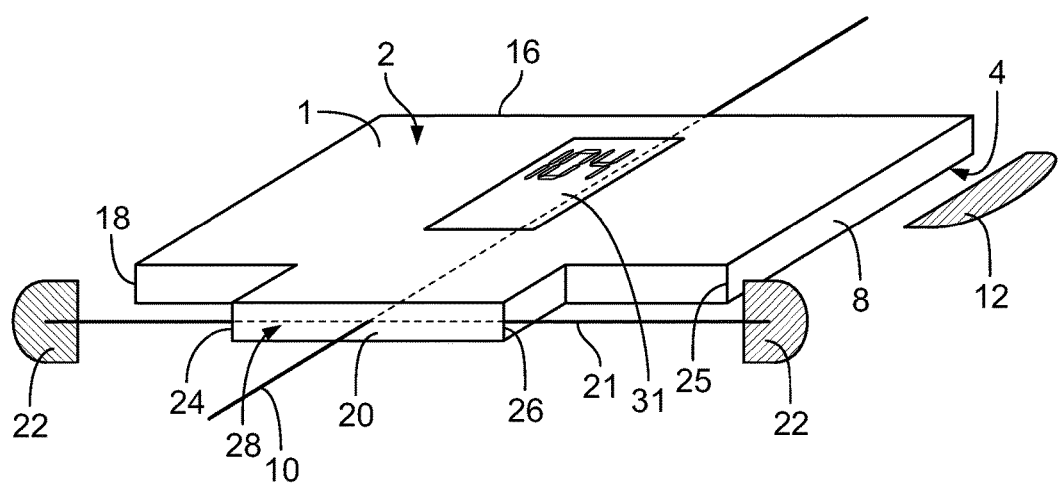
FIG. 8 shows a perspective schematic representation of another exemplary measurement device.
Figure 9:
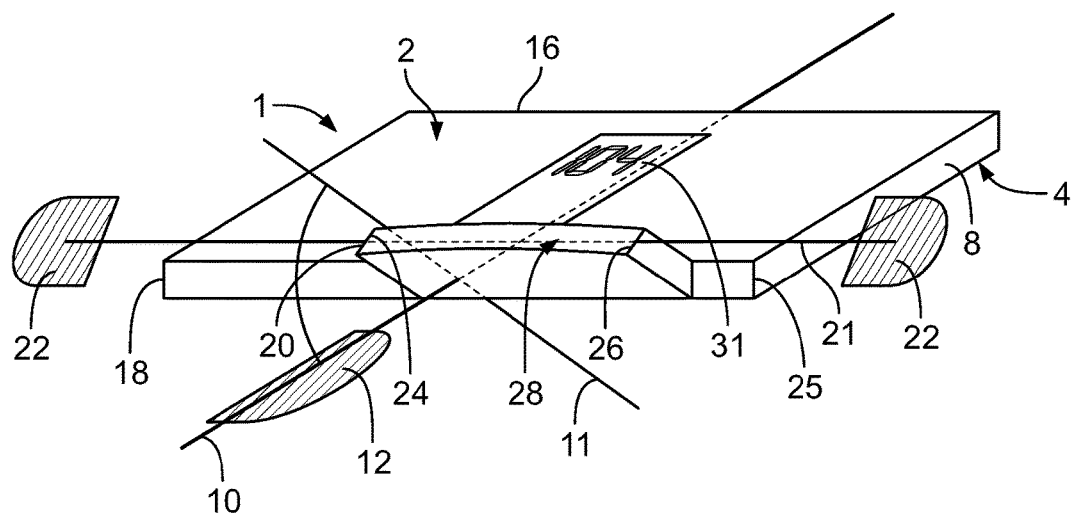
FIG. 9 shows a perspective schematic representation of another exemplary measurement device.
Figure 10:
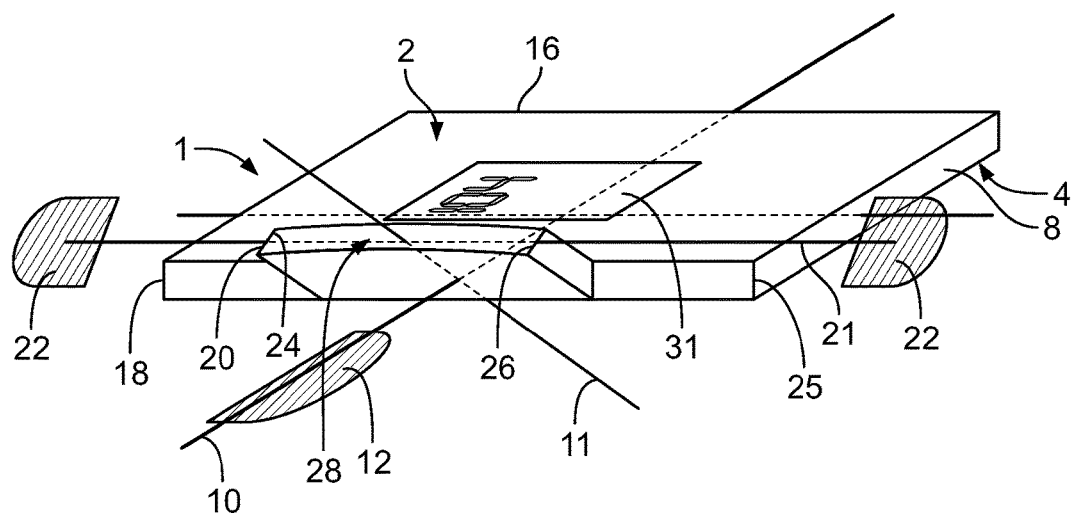
FIG. 10 shows a perspective schematic representation of another exemplary measurement device.

FIGS. 7 to 10 show embodiments in which only a section of the narrow side of the housing 1 on which the receiving surface 20 is disposed forms the receiving surface 20. This section therefore can be an exposed position. Specifically, FIGS. 7 and 9 to 10 show embodiments where the housing member on which the receiving surface 20 is disposed can be angled with respect to the remaining housing 1. The second device axis 11 can enclose an angle of about 60° with the device plane 12. Moreover, the axis 21 of the receiving surface 20 can enclose an angle of about 90° with the second device axis 11. FIG. 9 also shows an embodiment where the housing member on which the receiving surface 20 is disposed can be offset with respect to the remaining housing 1. As further shown in FIGS. 7 and 9 to 10, the receiving surface 20 can be curved with respect to the plane 22, which is spanned by the receiving surface 20.

In contrast, FIG. 8 shows an embodiment in which the receiving surface is not angled with respect to the remaining housing 1. The plane 22, which is spanned by the receiving surface 20, is essentially perpendicular to the device plane 12 in FIG. 8.

Figure 11:
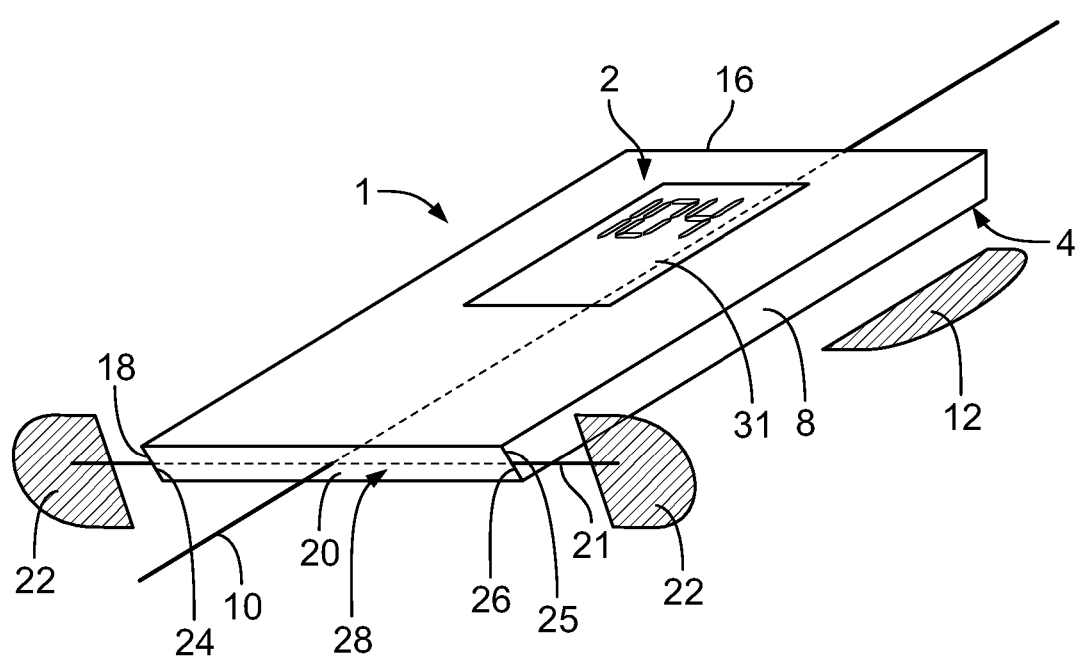
FIG. 11 shows a perspective schematic representation of another exemplary measurement device.

FIG. 11 shows another embodiment in which the entire narrow side of the housing 1 on which the receiving surface 20 is disposed forms the receiving surface 20. The axis 21 of the receiving surface 20 can enclose an angle of about 90° with the main device axis 10. The plane 22, which is spanned by the receiving surface 20, can be rotated by about −25° at the axis of the receiving surface 20.

Figure 12:
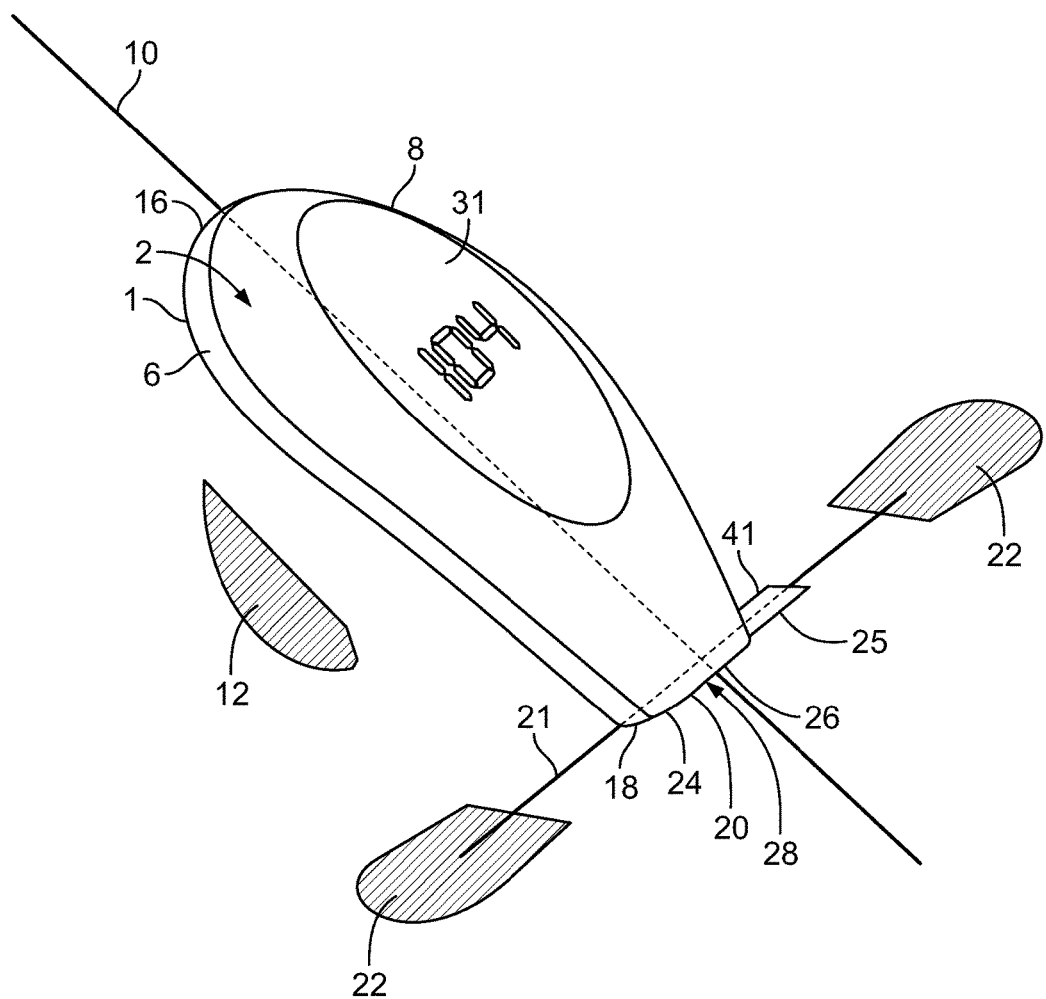
FIG. 12 shows a perspective schematic representation of another exemplary measurement device.

FIG. 12 shows an embodiment in which the base and top surface have an elliptical shape in combination with a rectangle. The edges that connect the transition corners from the rectangle to the ellipse of the base surface with the top surface are highly rounded such that the housing 1 has two narrow sides. The entire narrow side of the housing 1 on which the receiving surface 20 is disposed forms the receiving surface 20. The axis 21 of the receiving surface 20 can enclose an angle of about 90° with the main device axis 10. The top surface is convex, the base surface that is parallel thereto is concavely curved. The plane 22, which is spanned by the receiving surface 20, can be rotated by about −20° at the axis of the receiving surface 20.

Figure 13:
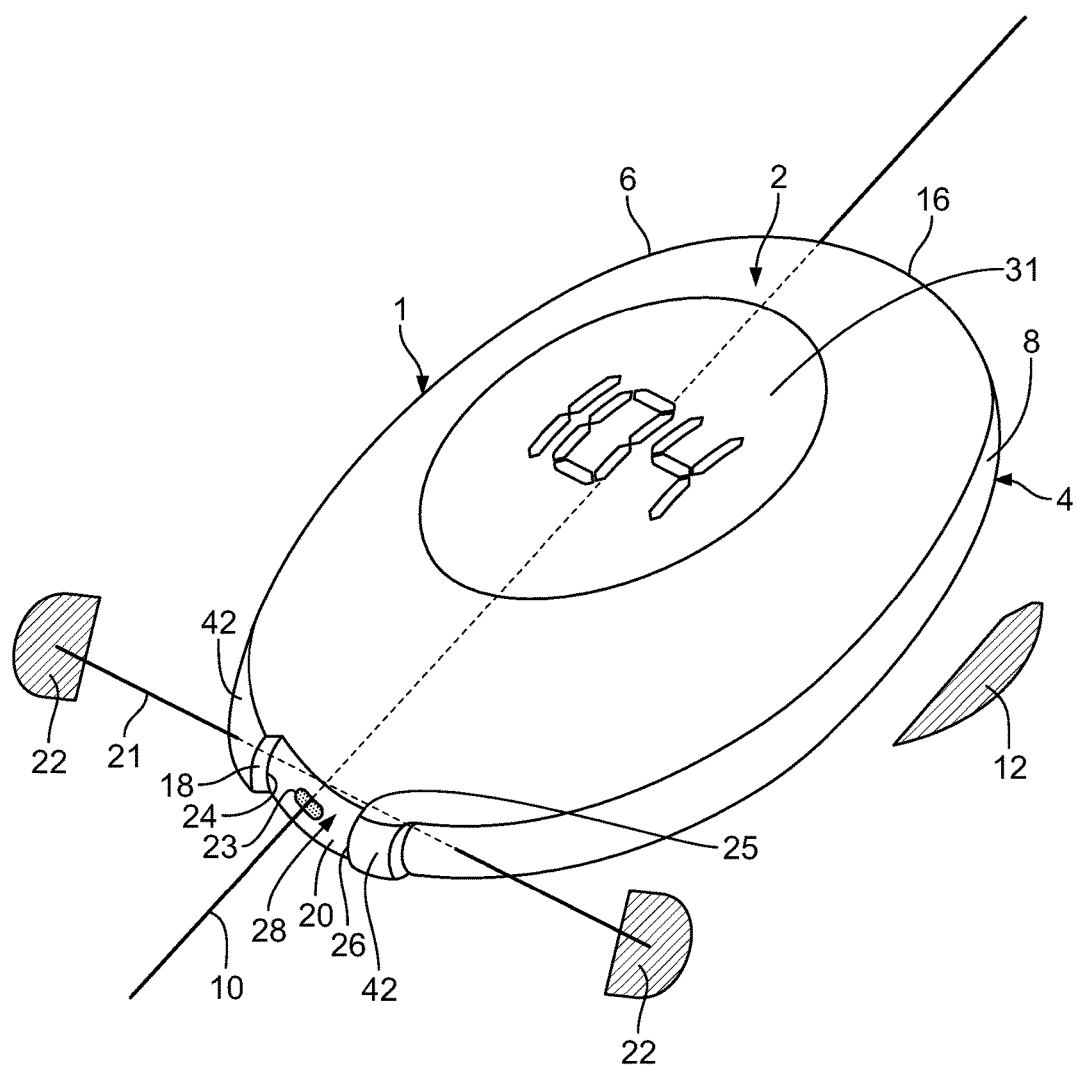
FIG. 13 shows a perspective schematic representation of another exemplary measurement device.
Figure 14:
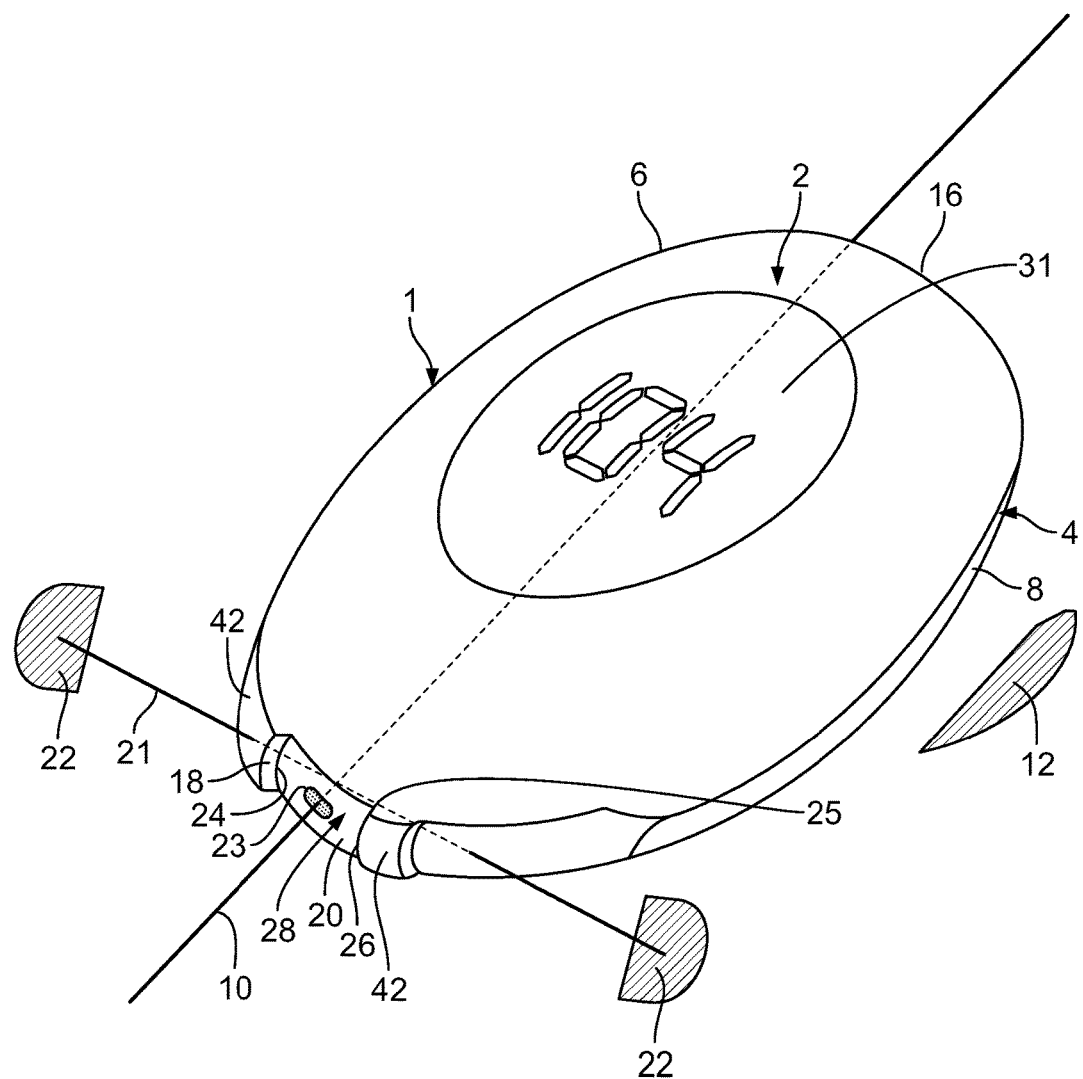
FIG. 14 shows a perspective schematic representation of another exemplary measurement device having a positioning device.

FIG. 13 shows an embodiment having a base and top surface with an elliptical shape such that the housing 1 has a narrow side. The receiving surface 20 is disposed on one section of the narrow side of the housing 1. The axis 21 of the receiving surface 20 can enclose an angle of about 90° with the main device axis 10. The top surface is convexly curved. Positioning devices 42 are designed as guide rails on both sides, which are formed as an integral unit and cover the receiving surface, and are disposed in the front section and in the handling section. The embodiment shown in FIG. 14 corresponds to that shown in FIG. 13, where the edges between the narrow side and the base surface and top surface outside the area of the narrow side, which forms the receiving surface 20, are rounded so that they are combined to form a single edge.

Figure 15:
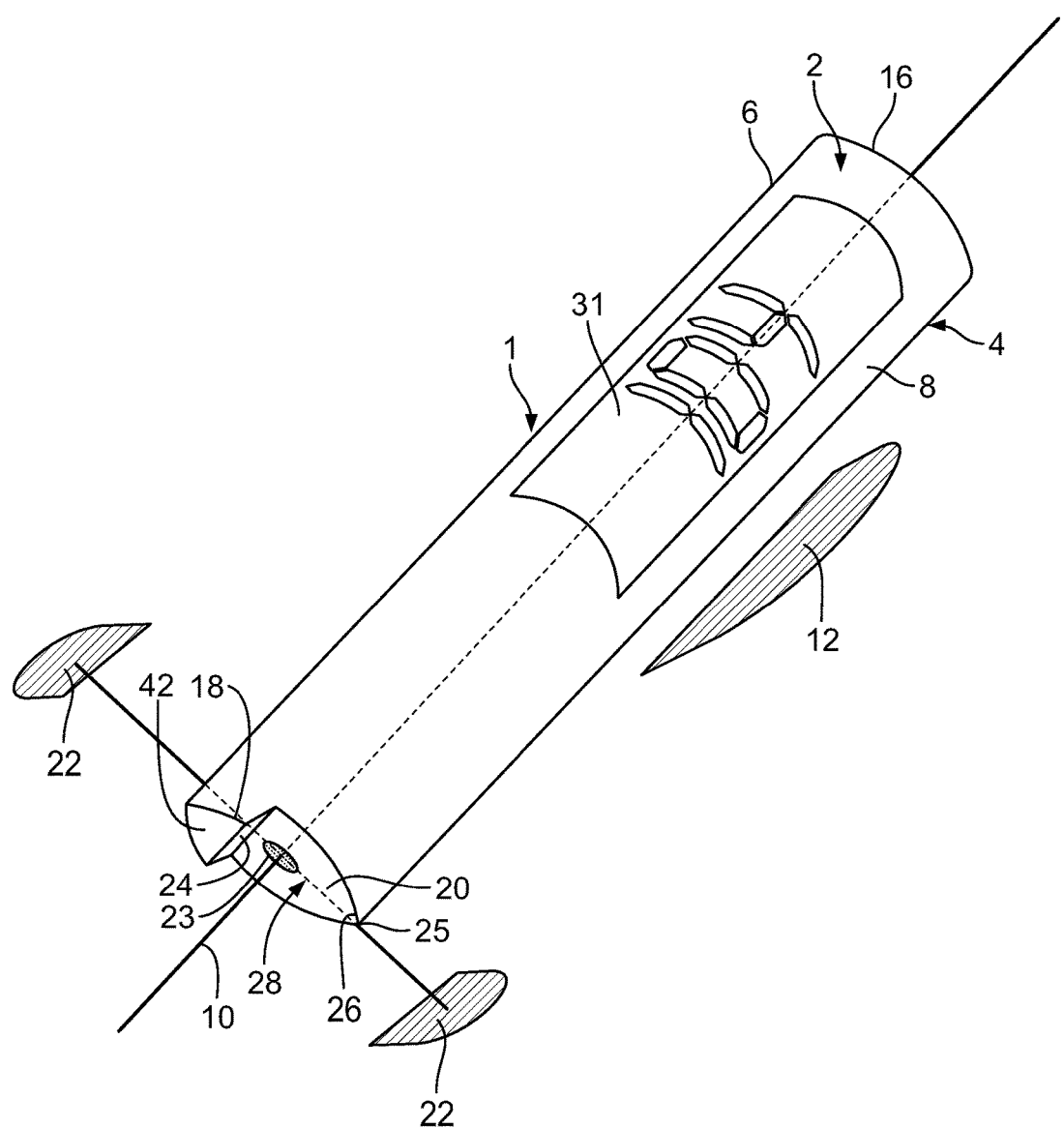
FIG. 15 shows a perspective schematic representation of another exemplary measurement device having a positioning device.

FIG. 15 shows an embodiment having a base surface and a top surface with a rectangular shape. The edges between both longitudinal narrow sides and the base and top surface are highly rounded so that in each case they combine to form a single edge. The housing 1 has two narrow sides. One of these narrow sides of the housing 1 forms the receiving surface 20. The plane 22, which is spanned by the receiving surface 20, can be rotated by about −10° at the axis 21 of the receiving surface 20. The top surface and the base surface can be convexly curved. The axis 21 of the receiving surface 20 can enclose an angle of about 90° with the main device axis 10. The positioning device 42 can be in the form of guide rails on either side (or both) and can be formed integrally and cover the receiving surface. They are disposed in the front section and in the handling section.

Figure 16:
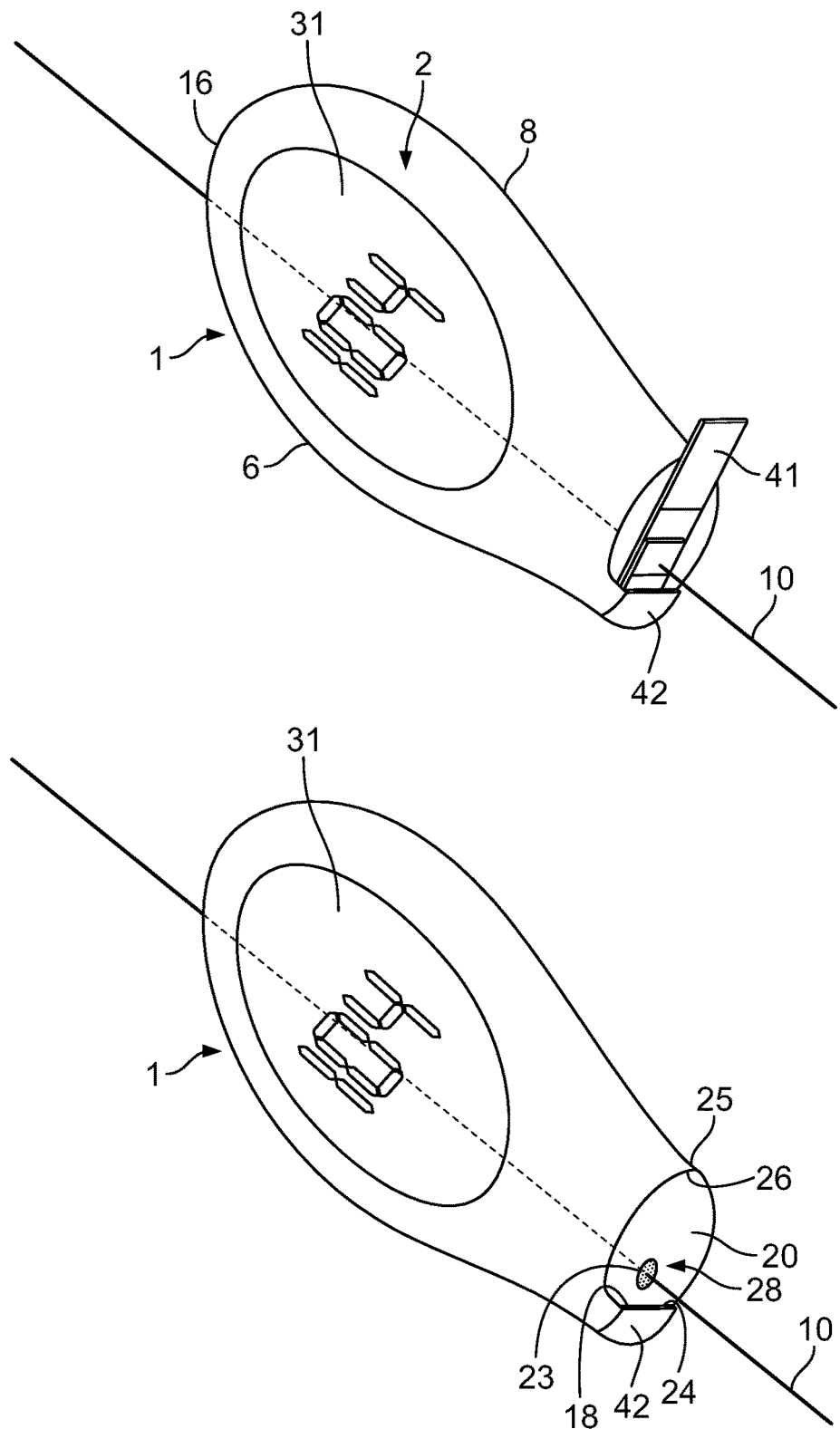
FIG. 16 shows a perspective schematic representation of another exemplary measurement device with and without a test element.

FIG. 16, like FIG. 12, shows an embodiment in which the base and top surface have an elliptical shape in combination with a rectangle. The edges, which bind the transition edges of the rectangle to the ellipse of the base surface with the top surface, can be highly rounded so that the housing 1 has two narrow sides. The edges between the narrow side and the base surface and the top surface outside the area of the narrow side, which forms the receiving surface 20, can be rounded in such a manner that they form an edgeless transition from the base surface to the top surface. The entire narrow side of the housing 1 on which the receiving surface 20 is disposed in this case forms the receiving surface 20. The axis 21 (not shown) of the receiving surface 20 can enclose an angle of about 90° with the main device axis 10. The plane 22 (not shown), which is spanned by the receiving surface 20, is perpendicular to the device plane 12 (not shown). The embodiment on the bottom of FIG. 16 is shown without a test element 41 so that the measuring opening 23 is visible. The same embodiment with the test element 41 is shown in the top of FIG. 16.

Figure 17:
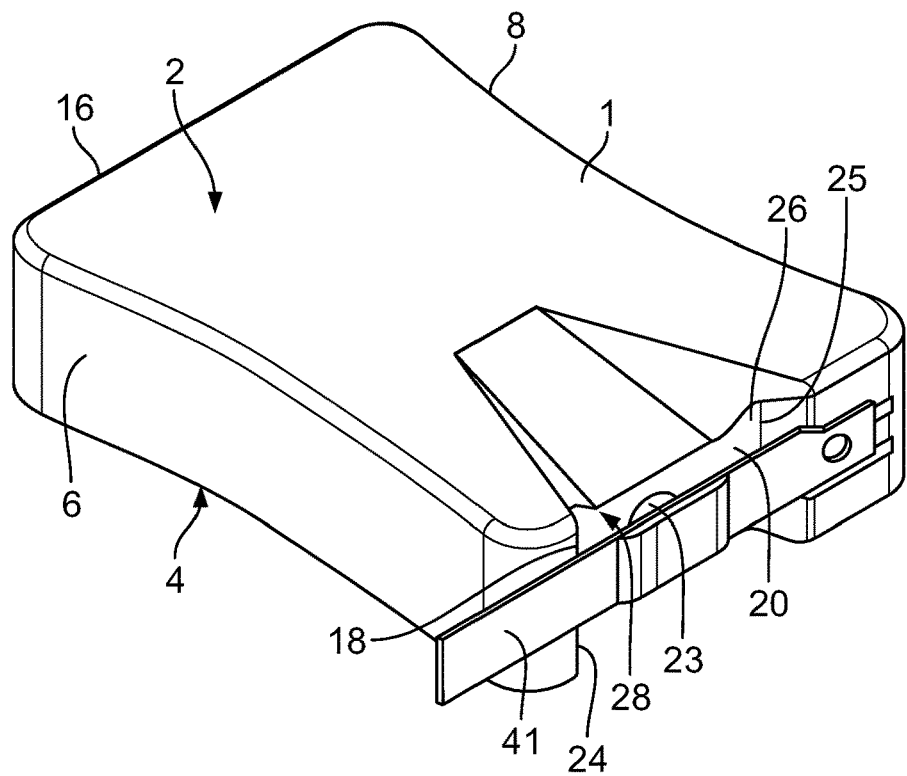
FIG. 17 shows a perspective schematic representation of another exemplary measurement device having a positioning device.

FIG. 17 shows an embodiment in which the base and top surface have a rectangular shape. The edges that connect the corners of the rectangle of the base surface with the top surface are rounded. The housing 1 has four narrow sides. The entire narrow side of the housing 1 on which the receiving surface 20 is disposed in this case forms the receiving surface 20. The axis 21 (not shown) of the receiving surface 20 can enclose an angle of about 90° with the main device axis 10. The plane 22 (not shown), which is spanned by the receiving surface 20 is perpendicular to the device plane 12 (not shown). The embodiment is shown with a test element 41 that does not yet lie in the positioning end position so that the measuring opening 23 is visible. The receiving surface 20 has a narrower form in the test field area than the test element.

Figure 18:
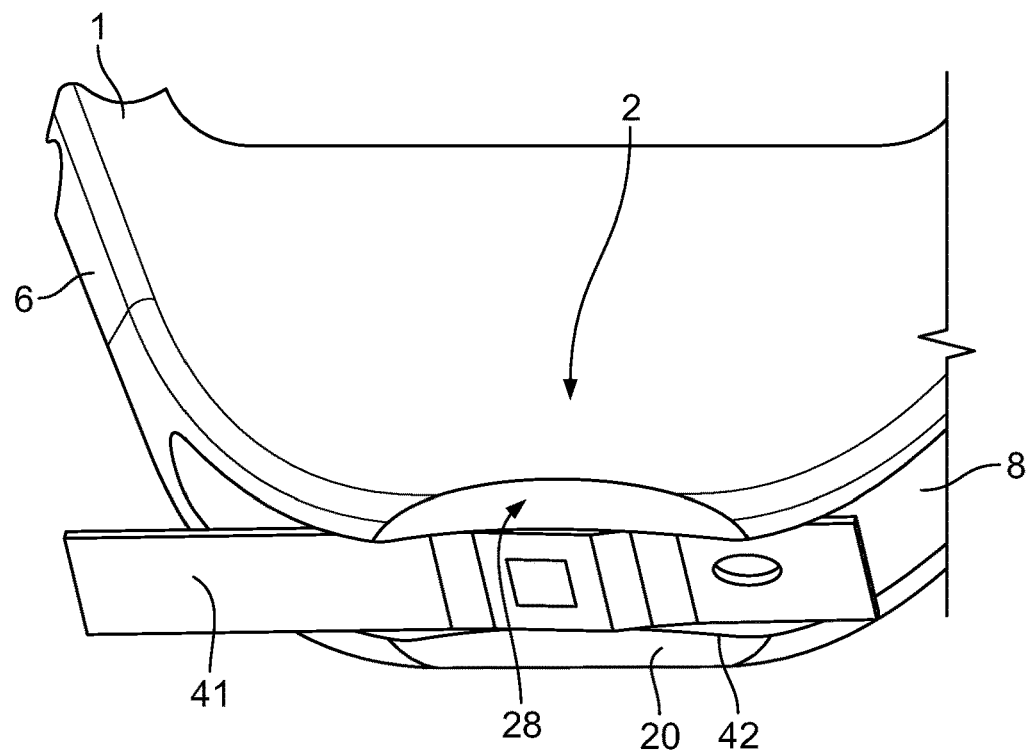
FIG. 18 shows a positioning device.

FIG. 18 shows an embodiment with guide rails as the positioning device 42 in the test field area. The guide rails partially cover the test element in the area in front of and behind the test field in order to prevent a vertical displacement of the test element.

Figure 19:
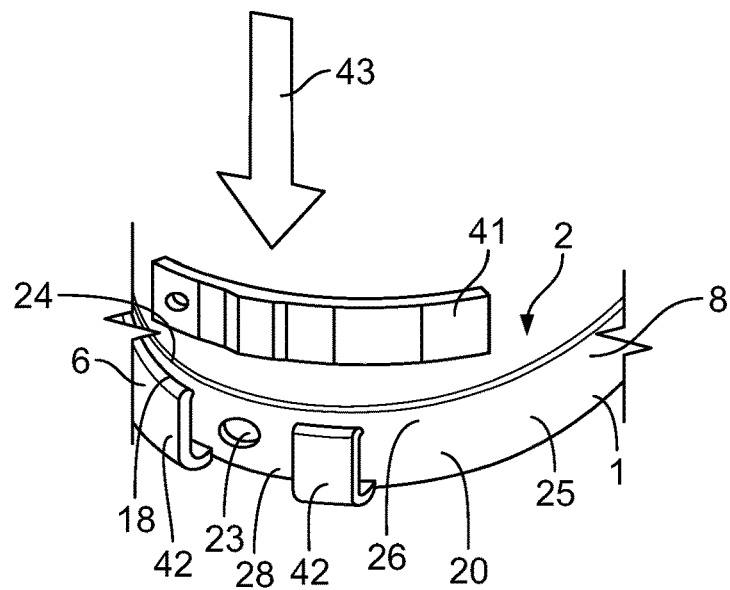
FIG. 19 shows another positioning device.

FIG. 19 shows an embodiment that includes a positioning device 42, which is in the form of one-sided guide rails in the front section and in the handling section. The guide rails cover the receiving surface 20 in these areas. Because the one-sided construction of the guide rails, the positioning process can take place from direction 43 of the front of the measurement device.

Figure 20:
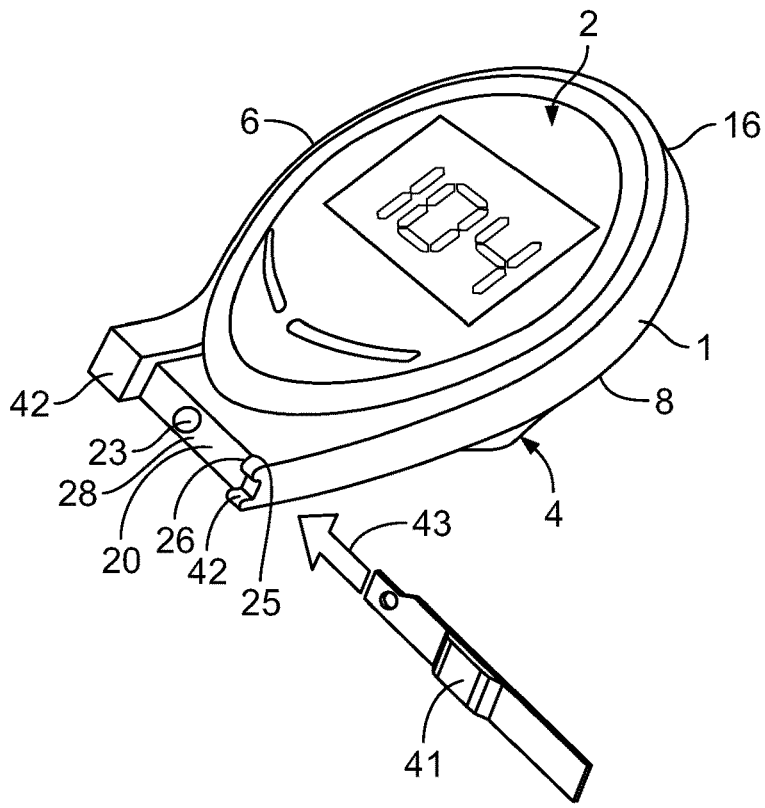
FIG. 20 shows a perspective schematic representation of another exemplary measurement device having a positioning device.

In contrast, FIG. 20 shows an embodiment that includes two positioning devices 42. A first positioning device in the front section is in the form of a double-sided guide rail, which covers the receiving surface 20. A holding pin is located under this covering cap, which is engaged with the corresponding opening of a test element 43 positioned in the measuring position. A second positioning device also is in the form of a two-sided guide rail but does not cover the receiving surface 20. The second positioning device is disposed at the handling end.

Figure 21:
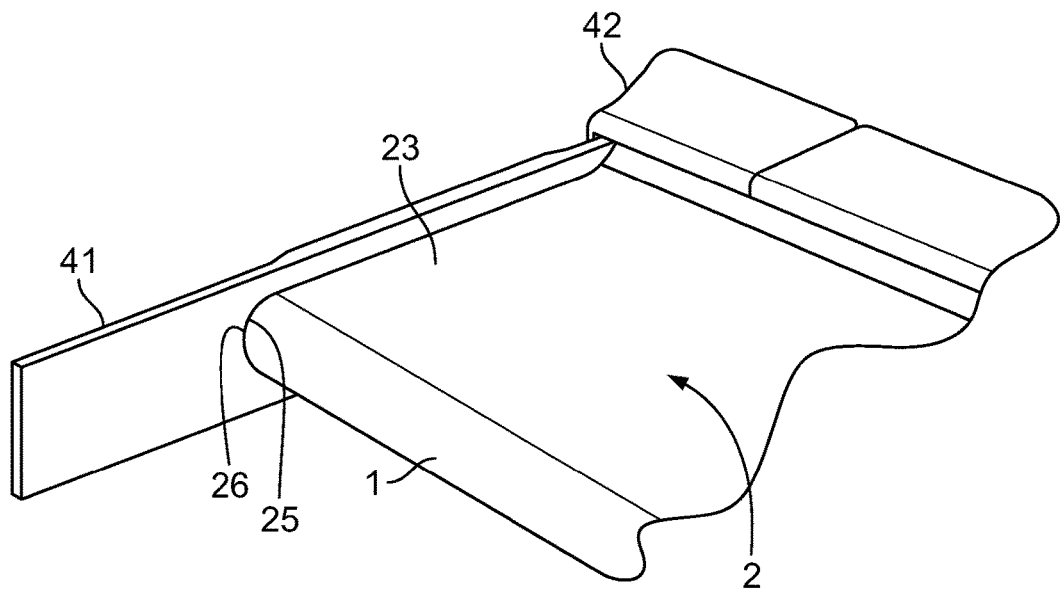
FIG. 21 shows a receiving surface.
Figure 22:
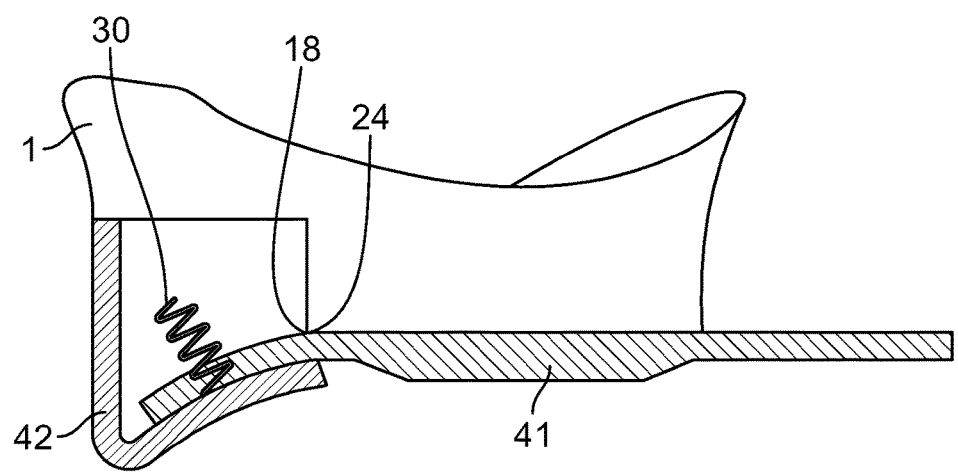
FIG. 22 shows another positioning device.
Figure 23:
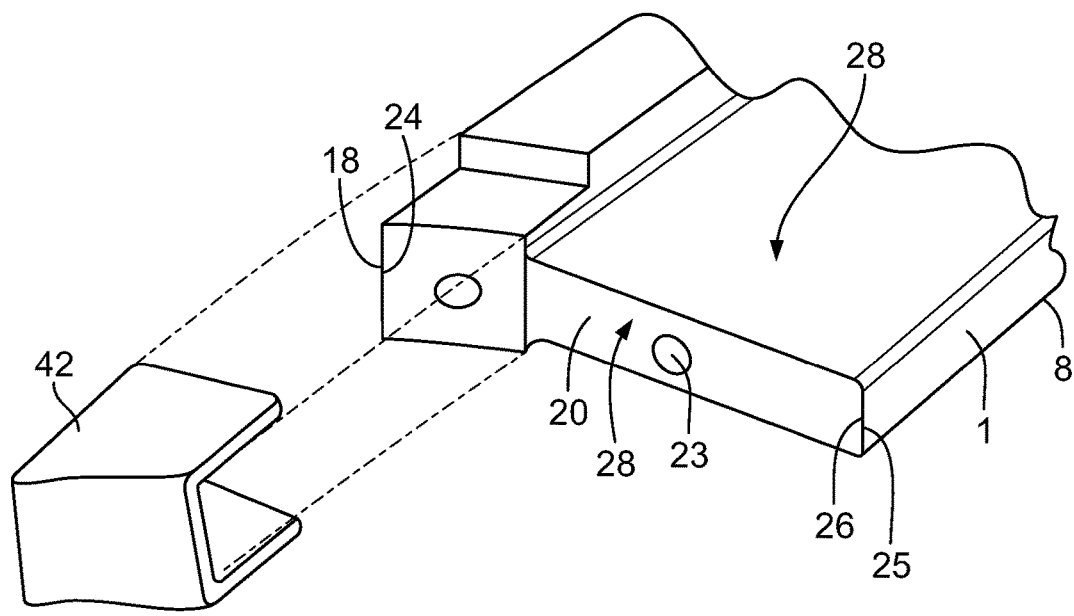
FIG. 23 shows the positioning device of FIG. 22 with and without a cover.
Figure 23:
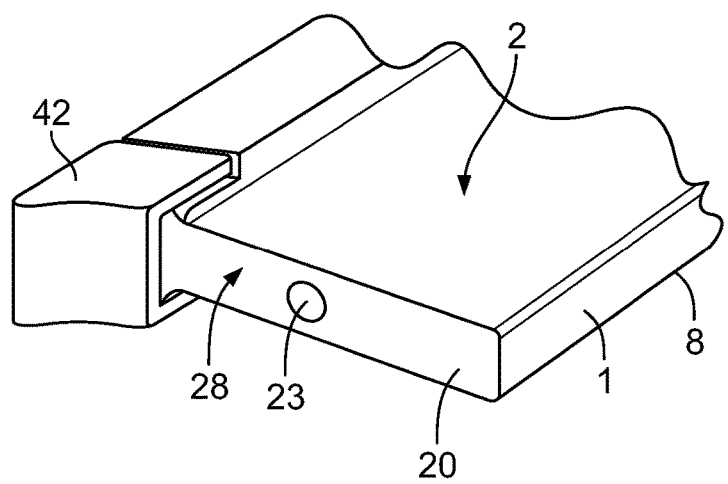

FIG. 21 shows a receiving surface 20, which is narrower than the test element 41 in the test field area and in the handling section. The receiving surface 20 is wider than the test element 41 in the area of the positioning device 42 at the front of the receiving surface 20. FIG. 22 shows such a positioning device 42 in a sectional view with a spring-loaded holding pin 30. FIG. 23 shows the removable cap 42*a* of the positioning device 42, as well as the receiving surface 20 with and without the cap 42*a*.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

LISTING OF REFERENCE NUMBERS

1. Housing
10. Main device axis
11. Second device axis
12. Device plane
20. Receiving surface
21. Longitudinal axis of the receiving surface
22. Plane spanning through the receiving surface
23. Measuring opening
31. Display on the front of the measurement device
41. Test element
42. Positioning device
43. Direction of positioning

The invention claimed is:

1. A portable diagnostic measurement device for determining at least one analytical parameter of a body fluid which is disposed on a carrier strip that has a surface for applying the body fluid, the measurement device comprising:
 a housing comprising a top surface, a base surface, a first side, an opposing second side, a narrow side, and an opposing side relative to the narrow side, wherein the first side defines a first end of the narrow side and the second side defines a second end of the narrow side;
 a receiving surface on the narrow side for receiving a test element that is in a form of the carrier strip, wherein the receiving surface comprises:
  a curved surface disposed on the narrow side of the housing proximate the second end; and
  a measuring opening disposed on the narrow side of the housing spaced from the first side and from the second side; and
 a positioning device covering the curved surface and providing a stop configured to receive a distal end of the carrier strip, the positioning device and the receiving surface arranged such that the carrier strip bends at least partially along the curved surface and extends over the measuring opening for measurement when the distal end of the carrier strip is received at the stop of the positioning device.

2. The device of claim 1 further comprising a measuring unit below the measuring opening.

3. The device of claim 2, wherein the measuring unit is an optical measuring unit.

4. The device of claim 1 further comprising another positioning device selected from a group consisting of: guide elements arranged on at least one side in a longitudinal direction of the receiving surface, a spring-loaded holding pin arranged under a removable or pivoted or foldable cap, and a raised rim of the measuring opening in the receiving surface.

* * * * *